United States Patent [19]
Scherz

[11] Patent Number: 5,183,460
[45] Date of Patent: Feb. 2, 1993

[54] WOUND DRESSING RETENTION APPARATUS

[76] Inventor: Hal C. Scherz, 4026 Caminito Terviso, San Diego, Calif. 92122

[21] Appl. No.: 877,237

[22] Filed: May 1, 1992

[51] Int. Cl.⁵ ............................................ A61F 13/00
[52] U.S. Cl. .................................. 602/79; 602/41; 602/58; 602/67; 128/844; 2/21
[58] Field of Search ........................ 602/41, 42, 58, 60, 602/61, 67, 70, 79; 128/844, 846; 2/21

[56] References Cited

U.S. PATENT DOCUMENTS

| | | | |
|---|---|---|---|
| 1,615,945 | 2/1927 | James | 602/42 |
| 1,980,486 | 11/1934 | King et al. | 128/882 |
| 2,431,203 | 11/1947 | Sebastian | 602/42 |
| 2,437,886 | 3/1948 | Millard et al. | 2/21 |
| 2,646,040 | 7/1953 | Stanton | 602/58 |
| 3,529,597 | 9/1970 | Fuzak | 602/58 |
| 3,971,374 | 7/1976 | Wagner | 602/58 |
| 4,341,209 | 7/1982 | Schaar | 602/58 |
| 4,754,750 | 7/1988 | Imonti | 602/58 |
| 4,875,476 | 10/1989 | Garcia | 602/65 |

*Primary Examiner*—Paul Prebilic
*Attorney, Agent, or Firm*—Anthony J. DeLaurentis

[57] ABSTRACT

A generally "L"-shaped bandage for use in retaining a dressing on a human penis and a method for using the bandage are disclosed. The bandage comprises a generally "L"-shaped cover member having an adhesive undersurface, wherein the longer leg of the "L" is comprised of a single strip of the cover member and the shorter leg of the "L" is comprised of three adjacent short strips of the cover member. In use, the three short strips which define the shorter leg of the "L" are adhered to the base of the penis and to the patient's skin adjacent the base of the penis, whereas the strip which defines the longer leg of the "L" is wrapped circumferentially around the shaft of the penis and around the dressing positioned on the penis.

10 Claims, 1 Drawing Sheet

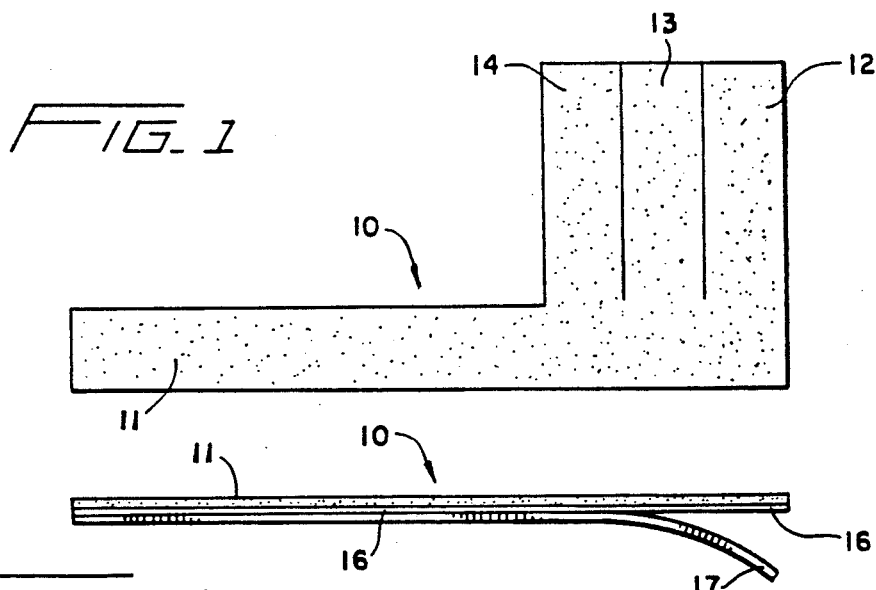
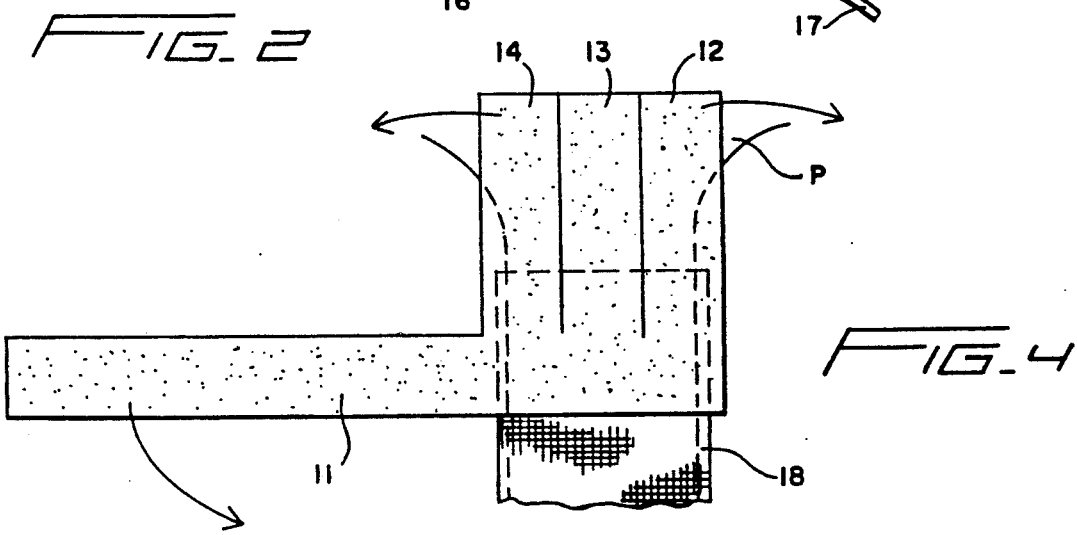
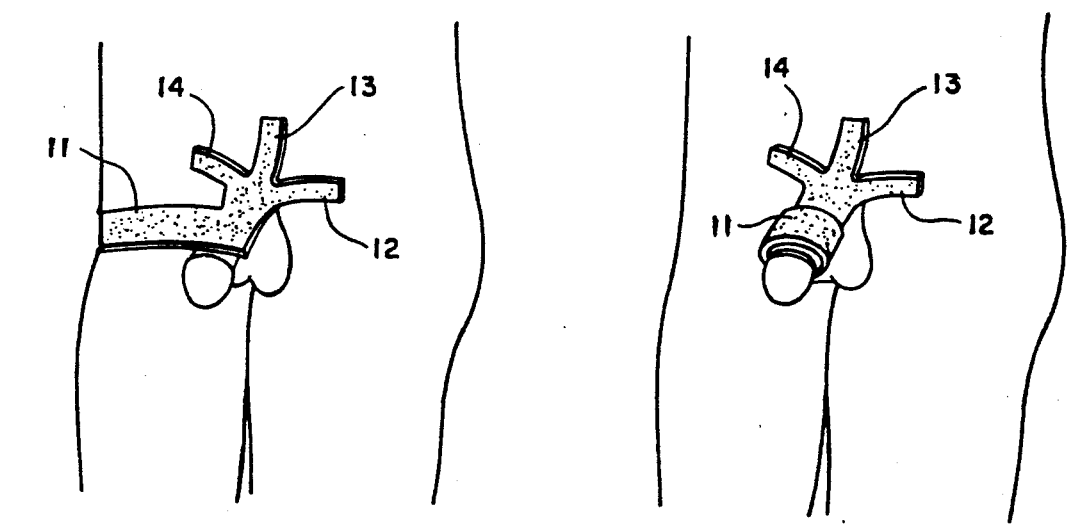

WOUND DRESSING RETENTION APPARATUS

BACKGROUND OF THE INVENTION

The present invention relates generally to wound dressings. More specifically, the invention is directed to a surgical bandage which is to be used in conjunction with gauze or other protective surgical dressing material on a human penis. The purpose of the surgical bandage of this invention is to retain the gauze or other dressing around the penis with adequate, but not excessive, force. The bandage can be used after any penile operation, including circumcision, or after an injury requiring an occlusive dressing.

At present, the inventor is not aware of any prior art that is particularly relevant to the surgical bandage of this invention. However, there are several U.S. patents of general interest which the inventor has reviewed. The following is a list of those patents:

U.S. Pat. No. 1,615,945, issued to James
U.S. Pat. No. 1,980,486, issued to King et al
U.S. Pat. No. 2,646,040, issued to Stanton
U.S. Pat. No. 3,529,597, issued to Fuzak
U.S. Pat. No. 3,971,374, issued to Wagner
U.S. Pat. No. 4,732,146, issued to Fasline et al
U.S. Pat. No. 4,870,977, issued to Imonti Among those patents listed above, the patent to James, U.S. Pat. No. 1,615,945, is the only patent which relates a bandage to be used on the penis. The James bandage, which is referred to as a surgical appliance, is used for obviating certain discomforts associated with a circumcision, and for holding the prepuce while undergoing healing after circumcision. In general, the James surgical appliance is comprised of a girdle, an absorbent and medicated pad, and a binding strip of antiseptic gauze.

In the patent to Imonti, U.S. Pat. No. 4,870,977, a surgical protector for raised wounds is disclosed. The surgical protector is specifically designed to protect an areola and/or nipple area of a woman's breast following a radical mastectomy. The surgical protector includes a con-shaped protector secured to a sterile pad. An adhesive system secures the pad and protector over the raised wound.

In the patent to Stanton, U.S. Pat. No. 2,464,040, a bandage for use in protecting protruding portions of the body is disclosed. The bandage includes an elongated rectangular cover member having an adhesive undersurface. A gauze pad covers the central region of the undersurface and slits in the cover member define longitudinally extending strips on either side of the gauze pad. The strips may be manipulated independently from each other so as to facilitate securement of the bandage to various protruding body portions such as a hand or finger.

The remaining listed patents are similarly directed to specific types of bandages. For example, the King et al patent, U.S. Pat. No. 1,980,486, relates to a surgical foot covering; the Fuzak patent, U.S. Pat. No. 3,529,597, relates to a fingertip bandage; and the Wagner patent, U.S. Pat. No. 3,971,374, relates to a padded bandage for the palm of one's hand.

None of the patents listed above relates to a surgical bandage which is particularly adapted for use in conjunction with gauze or other protective surgical dressing materials on the penis.

SUMMARY OF THE INVENTION

Penile dressings of the type which are used after any penile operation, including circumcision, or after an injury requiring an occlusive dressing, are difficult to maintain and often fall off. Accordingly, it is a primary object of the present invention to provide a surgical bandage that will readily retain a penile dressing in place.

Another object of the invention is to provide a surgical bandage that can be used after a circumcision or other penile operation or injury to retain gauze or other surgical dressing around a penis with adequate, yet not excessive, force to prevent the gauze or other dressing from falling off.

Yet another object is to provide a bandage which is specifically configured for use about the penis area and which can be quickly and easily applied to that area.

Still another object is to provide a surgical bandage which is adapted for use on the penis and which can be manufactured in sizes suitable for use on the penis of an infant, child or adult.

These and other objects and advantages of the present invention, as well as the advantages thereof over existing and prior art bandages, which will be apparent in view of the following specification, are accomplished by means hereinafter described and claimed.

In general, a surgical bandage for retaining a gauze or other dressing to the penis, according to the concept of the present invention, comprises a substantially "L"-shaped flexible cover member having an adhesive undersurface, wherein the cover member includes one elongated leg or strip defining the longer dimension of the "L" and three relatively shorter legs or strips extending perpendicularly from a first end of the elongated leg to define the shorter dimension of the "L". The three shorter legs are parallel to each other and are of substantially the same length, and the edge of the shorter leg closest to the first end of the elongated leg coincides with the first end of the elongated leg and forms an extension thereof. The adhesive undersurface of the cover member preferably is covered with a protective release layer which can be removed immediately prior to use, and the cover member preferably is comprised of a soft, foamed-type adhesive tape such as that marketed by 3M, Inc. under the trade designation Microfoam ®. In applying the bandage over a dressing on the penis, the shorter leg which is closest to the first end of the elongated leg is placed on the skin at the right hand base of the penis (when facing the patient's pubic area) and is secured upon the skin and upon the right hand base of the penis. The next adjacent shorter leg is applied similarly at the top of the base of the penis and the third shorter leg is applied on the left side of the penis. This leaves the elongated leg which is then wrapped circumferentially around the dressing which is on the penis.

The objects and advantages of the present invention will become apparent to those persons having ordinary skill in the art to which the invention pertains from the following description taken in conjunction with the accompanying drawings.

BRIEF DESCRIPTION OF THE DRAWINGS

FIG. 1 is a top plan view of a surgical bandage in accordance with the invention;

FIG. 2 is a front elevational view of the surgical bandage of FIG. 1;

FIG. 3 is a perspective view illustrating the surgical bandage of this invention as it is partially secured in place adjacent the base of the penis of a patient;

FIG. 4 is a schematic view illustrating the general direction in which the legs of the bandage are folded when the bandage is secured against the skin adjacent and circumferentially around the base of the penis; and FIG. 5 is perspective view illustrating the bandage of the invention fully secured around a penis.

DETAILED DESCRIPTION

Referring now to the drawing, and particularly to FIG. 1, the preferred embodiment of the invention is shown as comprising a substantially "L"-shaped surgical bandage 10 having an elongated leg or strip 11 and three shorter legs or strips 12, 13 and 14 extending at a right angle from one end therefrom. The bandage 10 comprises an upper cover layer having a conventional pressure sensitive adhesive layer 16 on its undersurface. The bandage may be formed from an adhesive coated fabric or plastic such as a conventional adhesive tape. However, in a preferred embodiment, the bandage is comprised of a soft, flexible tape material such as that marketed by 3M, Inc. under the trade designation Microfoam® adhesive tape. In preferred embodiments, the adhesive undersurface 16 of the bandage 10 would be covered by a suitable protective layer of release material 17, such as glasine paper or a non-stick plastic strip, which could be removed easily from the adhesive undersurface immediately prior to use.

As can be seen most clearly in FIG. 1, each of the shorter legs or strips 12, 13 and 14 is about one-third the length of the elongated leg 11; although somewhat shorter or longer lengths are contemplated.

In use, after the protective release layer 17 has been removed, the bandage 10 is placed adjacent the patient's pubic area such that the long leg or strip 11 lies generally at a right angle relative to the shaft of the penis P and such that the shorter legs 12, 13 and 14 are substantially parallel to the shaft (FIG. 4). The leg 12 is then folded over (FIG. 3) such it extends generally in the opposite direction as the long leg 11, whereafter the leg 12 is secured in adhesive contact with the base of the penis and the patient's skin adjacent the right side of the base of the penis. Next, the leg 13 adhesively secured against the top of the base of the penis and against the pubic area adjacent the top of the base of the penis, i.e. between the penis and navel. The leg 14 is then folded to the left, i.e. toward the length of the leg 11, and is adhesively secured in contact with the base of the penis and the groin area adjacent the left side of the base of the penis. This leaves the elongated leg 11 extending away from the base of the penis as shown in FIGS. 3 and 4. The leg 11 is then wrapped circumferentially around the penis or around a gauze or other dressing 18 (FIG. 4) that is on the penis so as to maintain the dressing in place. In this manner the bandage 10 can be used after a penile operation, such as a circumcision, to keep a gauze pad or other dressing from becoming dislodged or from otherwise falling off.

It will be appreciated that the bandage 10 can be made in various sizes so as to be useful for an infant, child or adult patient. It will be appreciated, also, that the bandage 10 can be used in conjunction with a variety of post-operative dressings including those customarily used after a circumcision, or with occlusive dressings used after an injury to the penis.

While only one embodiment of the invention has been shown, it will be obvious that various changes and modifications may be made by those skilled in the art without departing from the spirit and scape of the invention. Thus, it is intended that the claims which follow cover such obvious changes and modifications and their equivalents as broadly as the state of the prior art properly permits.

What is claimed is:

1. A bandage for retaining a dressing on a human penis which comprises:
 a substantially "L"-shaped flexible cover member having an adhesive undersurface, said cover member comprising one elongated leg member defining the longer dimension of the "L" and three adjacent short leg members extending perpendicularly from a first end of said elongated leg member such that said three short leg members together define the shorter dimension of the "L".

2. The bandage of claim 1, further comprising a protective release layer releasably bonded to said adhesive undersurface.

3. The bandage of claim 1, wherein said cover member comprises an adhesive backed foamed tape material.

4. The bandage of claim 1, wherein said cover member comprises an adhesive backed fabric material.

5. The bandage of claim 1, wherein said cover member comprises an adhesive backed plastic strip.

6. The bandage of claim 3, further comprising a protective release layer releasably bonded to said adhesive undersurface.

7. The bandage of claim 4, further comprising a protective release layer releasably bonded to said adhesive undersurface.

8. The bandage of claim 5, further comprising a protective release layer releasably bonded to said adhesive undersurface.

9. The bandage of claim 1, wherein each of said short leg members is about the same size, and wherein the shorter dimension of the "L" is about one-third the length of the longer dimension thereof.

10. A method of securing a dressing on the penis of a human patient, wherein the dressing comprises a substantially "L"-shaped flexible cover member having an adhesive undersurface, and wherein the cover member comprises one elongated leg member defining the longer dimension of the "L" and three adjacent short leg members extending perpendicularly from a first end of the elongated leg member such that the three short leg members together define the shorter dimension of the "L", which comprises;
 (a) positioning the dressing on the shaft of the human penis;
 (b) positioning said cover member adjacent the base of the penis (i) such that said elongated leg member extends in a first direction which is substantially perpendicular to the shaft of the penis, (ii) such that the ends of said short leg members which extend away from said first end of said elongated leg member point away from the head of the penis, and (iii) such that said adhesive undersurface faces the penis;
 (c) flexing a first short leg member, which is closest to said first end of said elongated leg member, in a second direction generally opposite to said first direction, and pressing said first short leg into adhesive contact with a first side of the base of the penis and with the patient's skin adjacent the base of the penis in said second direction;

(d) flexing a second short leg member, which is adjacent said first short leg member, and pressing said second short leg member into adhesive contact with the base of the penis and with the skin of the patient between the base of the penis and the area between the penis and navel;

(e) flexing the remaining short leg member generally in said first direction and pressing said remaining short leg member into adhesive contact with the side of the base of the penis facing said first direction and with the patient's skin adjacent the base of the penis in said first direction; and (f) wrapping said elongated leg member circumferentially around the penis and the dressing positioned on the penis to adhesively secure the dressing in place.

* * * * *